US007074233B1

(12) United States Patent
Gowda et al.

(10) Patent No.: US 7,074,233 B1
(45) Date of Patent: *Jul. 11, 2006

(54) METHOD FOR DELIVERING ENERGY TO TISSUE AND APPARATUS

(75) Inventors: Ashok Gowda, College Station, TX (US); Roger J. McNichols, Houston, TX (US); Massoud Motamedi, Houston, TX (US); Pankaj J. Pasricha, Houston, TX (US)

(73) Assignees: Board of Regents, The University of Texas System, Austin, TX (US); BioTex, Inc., Houston, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/877,811

(22) Filed: Jun. 25, 2004

Related U.S. Application Data

(63) Continuation of application No. 10/109,540, filed on Mar. 28, 2002, now Pat. No. 6,755,849.

(51) Int. Cl.
*A61N 5/067* (2006.01)

(52) U.S. Cl. .............................. 607/89; 606/2; 606/13; 607/88

(58) Field of Classification Search ................ 128/898; 607/89
See application file for complete search history.

(56) References Cited

U.S. PATENT DOCUMENTS

| 4,878,492 | A | * | 11/1989 | Sinofsky et al. ................ 606/7 |
| 5,100,429 | A | | 3/1992 | Sinofsky et al. |
| 5,609,591 | A | | 3/1997 | Daikuzono |
| 5,623,940 | A | | 4/1997 | Daikuzono |
| 6,044,846 | A | | 4/2000 | Edwards |
| 6,073,052 | A | | 6/2000 | Zelickson et al. |
| 6,224,590 | B1 | | 5/2001 | Daikuzono |
| 6,283,959 | B1 | | 9/2001 | Lalonde et al. |
| 6,321,121 | B1 | | 11/2001 | Zelickson et al. |
| 6,575,966 | B1 | | 6/2003 | Lane et al. |
| 6,755,849 | B1 | | 6/2004 | Gowda et al. |
| 2002/0077625 | A1 | * | 6/2002 | Lev ............................. 606/27 |
| 2002/0115991 | A1 | | 8/2002 | Edwards |

OTHER PUBLICATIONS

McGouran et al., "A Laser-Induced Scar at the Cardia Increases the Yield Pressure of the Lower Esophageal Sphincter," *Gastrointest. Endosc.*, 36(5):439-443 (1990).

* cited by examiner

*Primary Examiner*—Henry M Johnson, III
(74) *Attorney, Agent, or Firm*—Rogalskyj & Weyand, LLP (57) ABSTRACT

Disclosed is a method for delivering energy to a tissue. The method includes providing an apparatus which includes an energy delivery component and an inflatable member disposed around the energy delivery component. At a minimum, the inflatable member is constructed of a flexible inner wall and a flexible outer wall, which, taken together, enclose a cavity therebetween. The inflatable member is expanded such that the inflatable member's outer wall contacts the tissue's surface. Cooling fluid is disposed in the cavity, and energy is delivered to the energy delivery component so that at least a portion of the energy delivered to the energy delivery component passes through the inflatable member's inner wall, through the cooling fluid disposed in the cavity, through the inflatable member's outer wall, and into the tissue. Various apparatus suitable for use in delivering energy to tissues are also disclosed, as is a method for treating GERD or otherwise reducing reflux of a subject's stomach contents into the subject's esophagus.

13 Claims, 9 Drawing Sheets

METHOD FOR DELIVERING ENERGY TO TISSUE AND APPARATUS

This application is a continuation of U.S. patent application Ser. No. 10/109,540, filed Mar. 28, 2002, now U.S. Pat. No. 6,755,849.

FIELD OF THE INVENTION

The invention is directed, in part, to a method and apparatus for thermal corrective treatment of esophageal sphincters to prevent or reduce incidence of gastroesophageal reflux.

BACKGROUND OF THE INVENTION

Gastroesophageal reflux disease ("GERD") is a condition in which the lower esophageal sphincter ("LES") is unable to function properly resulting in the reflux of stomach secretions, in the forms of acid and enzymes, into the esophagus. Exposure of the esophagus epithelium to these secretions, where there is no anatomical or physiological protection, results in deterioration and/or destruction of the lining of the esophagus lumen. GERD is a major health care problem in the United States. 44% of Americans experience monthly heartburn, and it has been estimated that 5–10% of the US population (14–28 million adults) suffer from "significant (daily) heartburn". There is a wide range in ages of the afflicted, but GERD is more common in individuals over the age of 50. In fact, GERD appears to be second only to psychiatric illness in terms of its effect on overall quality of life. Symptoms of this condition include chronic indigestion or heartburn, inability to eat, discomfort in swallowing, asthma, regurgitation, and chest pain. Prolonged exposure can lead to esophagitis or linear streaking and ulceration of the esophagus epithelium. In the long term, esophagitis can lead to a condition known as Barrett's esophagus, in which there is extreme damage to the lining of the esophagus and which is believed to be a pre-cursor to cancer of the esophagus. Barrett's esophagus has attained national importance as it is associated with an increased risk of adenocarcinoma of the gastroesophageal junction, which has become the most rapidly growing cancer in middle-aged white males. In fact, in a recent article in the New England Journal of Medicine, researchers reported that GERD, even when treated with medication, can lead to an increased risk of esophageal cancer (Lagergren et al., "Symptomatic Gastroesophageal Reflux as a Risk Factor for Esophageal Adenocarcinoma," *New England Journal of Medicine*, 340(11): 825–31 (1999)). It is clear, therefore, that GERD represents a significant medical concern. Consequently, it has been the target of several therapeutic approaches.

There are several different treatment options for GERD for varying stages of disease progression and discomfort experienced by the patient. The least aggressive approach is modification of lifestyle and diet. Changes are made to daily eating habits and posture along with altering food consumption. These changes are intended to diminish secretion of acid and enzymes in the stomach. This approach does not address the sphincter dysfunction and, in most cases, is used in conjunction with other treatment options. The results from non-surgical options are not statistically appealing. Only a small percentage of the patients undergoing these treatments avoid the need for future surgical treatment once the disease and its symptoms have progressed. Moreover, these methods call for an overall life adjustment and can result in an enormous life-long financial burden for the patient without correcting or repairing the physiological malfunction.

The mainstay of current therapy is still pharmacological suppression of acid production, which is effective in 90% of patients. There are a wide range of new medications for treatment of reflux disease including omeprazole and other proton pump inhibitors. However, because GERD is a chronic disease, treatment with medication must be continuous, and symptoms recur in 80% when treatment with medication is terminated. Further, the most effective drugs (proton pump inhibitors) are also the most expensive, and the cost of treatment with medication is between $1500–2000 per patient per year. Overall, it has been estimated that over $14 billion is spent annually on heartburn medications.

There are several invasive treatment procedures that address the dysfunction of the sphincter to correct reflux disorders. Fundoplication is a surgical procedure where the fundus of the stomach is wrapped around the gastroesophageal junction and sutured to the esophagus. The intragastric pressure in the fundus is translated to the sphincter enabling it to resist the reflux of the stomach contents into the esophagus. The most common fundoplication procedure currently used is the Nissen procedure. The Nissen approach involves complete wrapping of the gastroesophageal junction with the fundus. This treatment corrects the malfunction of the sphincter but is an invasive surgery, requiring general anesthesia and hospitalization (even with the increasingly popular laparascopic approach), and may result in side-effects, such as gas-bloat syndrome. In fact, a study evaluating 344 patients over a 10 year period found that the morbidity and mortality rates for this procedure were 17% and 1%, respectively (Urschel, "Complications of Antireflux Surgery," *Am. J. Surg.*, 166(1):68–70 (1993)).

A less invasive method of performing fundoplication is reported in U.S. Pat. No. 5,088,979 to Filipi et al. This method involves inserting a device containing a plurality of needles into the esophagus. Once extended, the needles are designed to engage the esophagus and allow the operator to fold the wall beyond the gastroesophageal junction. A stapling device, introduced percutaneously through a channel in the stomach, is used to secure the gastroesophageal junction to the surrounding stomach wall. U.S. Pat. No. 5,676,674 to Bolanos et al. describes a modified version of the approach above, whereby the invagination of the esophageal wall as well as fastening are both performed transorally. All of these procedures are still traumatic to the LES and result in risks associated with gastroesophageal leaks, infection, and foreign body reactions.

Most of the commonly performed surgical procedures alleviate the condition of reflux through the correction of the sphincter dysfunction at a cost of creating more potential complications. These procedures are invasive and must be performed by specially trained doctors. Recovery time can last up to several weeks, translating into significant cost and inconvenience for the patient. Even with the prospect of a substantial improvement in quality of life, most patients elect not to have corrective surgical procedures due to their invasive nature.

Other less invasive thermal approaches have been investigated for creating lesions in the LES which provide improved competence for the sphincter. McGouran et al., "A Laser-Induced Scar at the Cardia Increases the Yield Pressure of the Lower Esophageal Sphincter," *Gastrointest. Endosc.*, 36(5):439–443 (1990) describes the use of a Nd:YAG laser to produce fibrous scar at the cardia in a canine model. However, applying thermal energy in the fashion described is accompanied by significant risks, as evidenced by one subject dying from gastric perforation 10 days after lasing.

Yet another thermal approach is described in U.S. Pat. No. 6,044,846 to Edwards. In this procedure, a device is introduced to the gastroesophageal junction endoscopically where a balloon is then inflated. The procedure further involves inserting RF electrodes into the junction through the epithelium and passing a cold fluid over the balloon to protect the epithelial lumen of the esophagus. The electrodes deliver RF energy which induces thermal coagulation of muscular tissue in the esophagus. This process is then repeated multiple times along the length of the junction over a period of about 40 minutes. The coagulated tissue provides support for the sphincter, allowing it to resist the reflux of the stomach contents into the esophagus. However, this procedure requires insertion of the RF electrodes into the wall of the esophagus and, therefore, is still traumatic to the mucosal layer of the LES. Also, the procedure requires multiple treatments along a length of the LES to effect the desired lesion. Precise positioning during the multiple treatments must be maintained to prevent overlap of thermally treated tissues.

For these and other reasons, a need remains for alternative methods for correction of GERD. The present invention, in part, is directed to meeting this need.

SUMMARY OF THE INVENTION

The present invention relates to a method for delivering energy to a tissue. The method includes providing an apparatus which includes an energy delivery component and an inflatable member disposed around the energy delivery component. At a minimum, the inflatable member is constructed of a flexible inner wall and a flexible outer wall, which, taken together, enclose a cavity therebetween. The inflatable member is expanded such that the inflatable member's outer wall contacts the tissue's surface. Cooling fluid is disposed in the cavity, and energy is delivered to the energy delivery component so that at least a portion of the energy delivered to the energy delivery component passes through the inflatable member's inner wall, through the cooling fluid disposed in the cavity, through the inflatable member's outer wall, and into the tissue.

The present invention also relates to an apparatus which includes an inflatable member and an energy delivery component disposed within the inflatable member. The inflatable member includes a flexible inner wall and a flexible outer wall. The inflatable member's inner wall and the inflatable member's outer wall enclose a cavity therebetween, and the cavity includes an inlet and an outlet.

The present invention also relates to an apparatus which includes a housing and an inflatable member disposed radially around the housing. The inflatable member includes a flexible inner wall and a flexible outer wall. The inflatable member's inner wall and the inflatable member's outer wall enclose a cavity therebetween, and the cavity includes an inlet and an outlet. The housing includes a first lumen and a second lumen. The first lumen is in fluid communication with one of the cavity's inlet and outlet, and the second lumen is in fluid communication with the other of the cavity's inlet and outlet.

The present invention also relates to a method for reducing reflux of a subject's stomach contents into the subject's esophagus. The method includes cooling a mucosal layer of the subject's lower esophageal sphincter and exposing the subject's lower esophageal sphincter to laser radiation under conditions effective to cause cellular necrosis in the subject's lower esophageal sphincter and under conditions effective to cause the formation of a thermal lesion in the subject's lower esophageal sphincter, the thermal lesion being substantially confined to the lower esophageal sphincter's smooth muscle layer.

The present invention also relates to a method for delivering energy to a tissue which includes a surface tissue layer and one or more subsurface tissue layers lying beneath the surface tissue layer. The method includes cooling at least the tissue's surface tissue layer with a cooling fluid and exposing the tissue to laser energy such that the laser energy is preferentially absorbed by at least one of the subsurface tissue layers.

DETAILED DESCRIPTION OF THE INVENTION

The present invention relates to an apparatus that is useful for the treatment of GERD and other conditions. The apparatus includes an energy delivery component and an inflatable member disposed around the energy delivery component. For purposes of the present invention, the inflatable member is to be deemed "disposed around" the energy delivery component if at least about 50% (e.g., at least about 70%, at least about 80%, at least about 85%, at least about 90%, and/or at least about 95%) of the energy emitted by the energy delivery component passes through the inflatable member prior to exiting the apparatus. The inflatable member includes a flexible inner wall and a flexible outer wall. The inflatable member's inner wall and the inflatable member's outer wall enclose a cavity therebetween, and the cavity includes an inlet and an outlet.

The energy delivery component can itself be an energy source, or it can be coupled to an energy source which is external to the apparatus. Suitable energy sources that can be used in the practice of the present invention include, for example, electromagnetic energy sources, such as optical energy sources, radiofrequency energy sources, microwave energy sources, and the like. As used herein, optical energy sources are meant to include ultraviolet energy sources, visible-light energy sources, and infrared energy sources. As indicated above, the energy delivery component can be coupled to an energy source external to the apparatus. For example, in the case where the energy source is an optical energy source, the energy delivery component can be a waveguide (e.g., a fiber optic) which is optically coupled to the optical energy source. Suitable optical energy sources for use in connection with the present invention include, for example, filament bulbs, a gas discharge bulbs, and arc lamps, as well as sources of monochromatic optical energy, such as lasers.

Figure 1A:
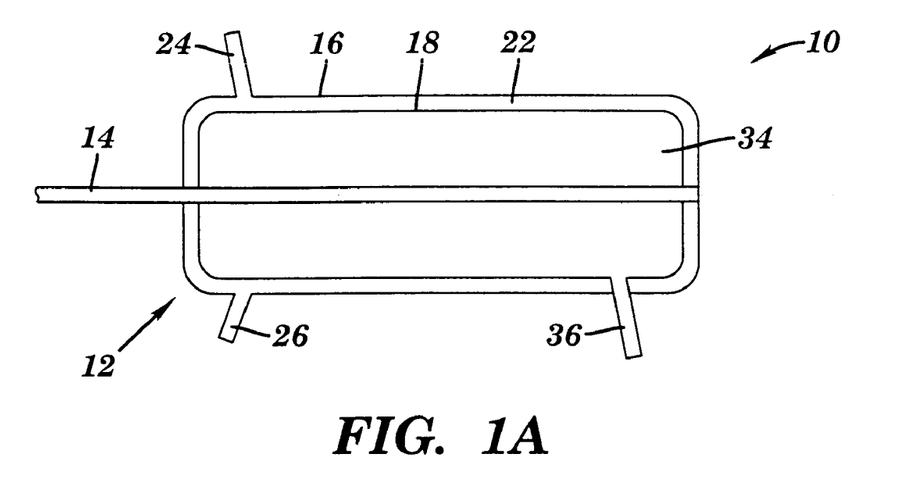
FIGS. 1A and 1B are longitudinal sectional views of various embodiments of apparatus according to the present invention.

One apparatus in accordance with the present invention is illustrated in FIG. 1A. Referring to FIG. 1A, apparatus 10 is shown as including energy delivery component 14 and inflatable member 12 disposed around energy delivery component 14. Inflatable member 12 includes flexible outer wall 16 and flexible inner wall 18. Inner wall 18 and outer wall 16 of inflatable member 12 enclose cavity 22, and cavity 22 includes inlet 24 and outlet 26.

Figure 1B:
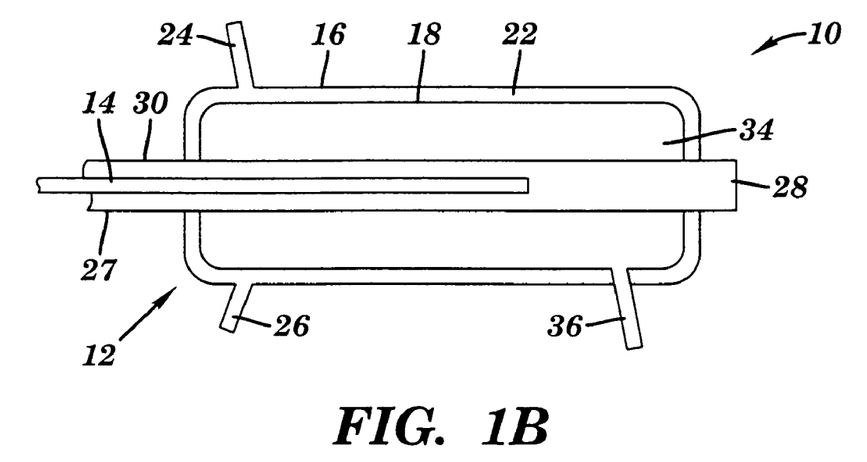

Another apparatus in accordance with the present invention is illustrated in FIG. 1B. Referring to FIG. 1B, apparatus 10 is shown as including housing 27 and inflatable member 12 disposed around housing 27. Housing 27 includes lumen 28, and energy source 14 disposed in lumen 28. Inflatable member 12 includes flexible outer wall 16 and flexible inner wall 18. Inner wall 18 and outer wall 16 of inflatable member 12 enclose cavity 22, and cavity 22 includes inlet 24 and outlet 26.

The apparatus described in FIGS. 1A and 1B are operated by increasing the pressure inside inflatable member 12 (e.g., by increasing the pressure inside space 34 enclosed by flexible inner wall 18 and outer surface 30 of housing 27) so that inflatable member 12 inflates or otherwise expands. This can be carried out, for example, by introducing a fluid (such as a gas or a liquid or both), under pressure, into space 34, for example, via port 36.

FIGS. 2A–2E illustrate yet other apparatus in accordance with the present invention, as well as various subsystems that can be employed in apparatus of the present invention.

Figure 2A:
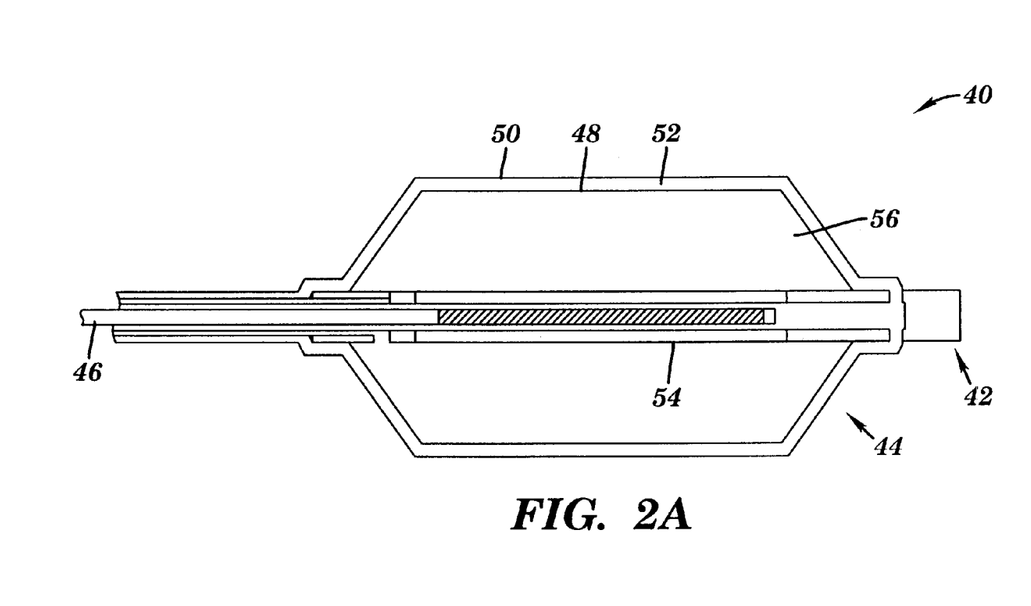
FIGS. 2A–2E are longitudinal sectional views of various embodiments of apparatus according to the present invention and various component parts of such apparatus.

As shown in FIG. 2A, thermal delivery apparatus 40 includes catheter component 42, inflatable member 44, and energy delivery component 46. Inflatable member 44 includes flexible inner wall 48 and flexible outer wall 50, which together enclose cavity 52. Flexible inner wall 48 and outer surface 54 of catheter component 42 enclose interior space 56, such that inflation of interior space 56 would cause inflatable member 44 to expand.

Figure 2B:
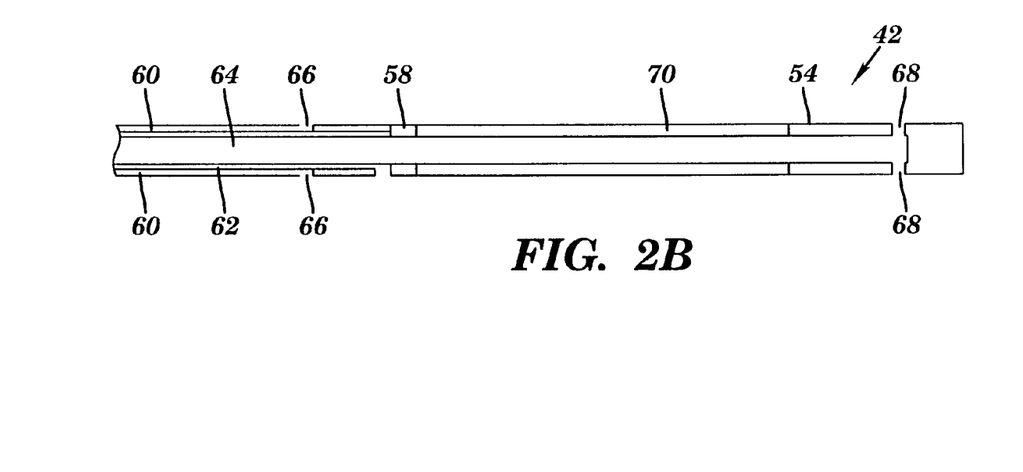

FIG. 2B details one suitable configuration for catheter component 42, particularly for use in connection with the delivery of laser energy. Referring now to FIG. 2B, catheter component 42 includes tubular housing 58. Tubular housing 58 contains one or more lumens 60 for delivery of cooling fluid to (or return of cooling fluid from) cavity 52, one or more lumens 62 for delivery of air or liquid to interior space 56 of inflatable member 44 (shown in FIG. 2A), and a central lumen 64 for housing laser energy delivery component 46 and for return (or delivery) of cooling fluid (discussed further below). Lumens 60, used for delivery of cooling fluid, contain exit openings 66 on outer surface 54 of tubular housing 58. Although FIG. 2B shows the presence of two such exit openings 66 located just distal to the proximal end of tubular housing 58, it will be appreciated that one, two, three, or any number of such exit openings 66 can be used and that their position is not particularly critical to the practice of the present invention. Central lumen 64 exits at one or more openings 68 on outer surface 54 of tubular housing 58 at a location distal to exit openings 66. The central portion of the tubular housing 58 contains optically transparent window section 70 which facilitates delivery of laser light through tubular housing 58. Tubular housing 58 can be constructed of any suitable material, for example, flexible, medical grade tubing made from polyimides, polyethlenes, polypropylenes, polyurethanes, silicones, nylon, PVC, PET, PTFE, ABS, PC PES, PEEK, FEP, and other biocompatible polymers.

Figure 2C:
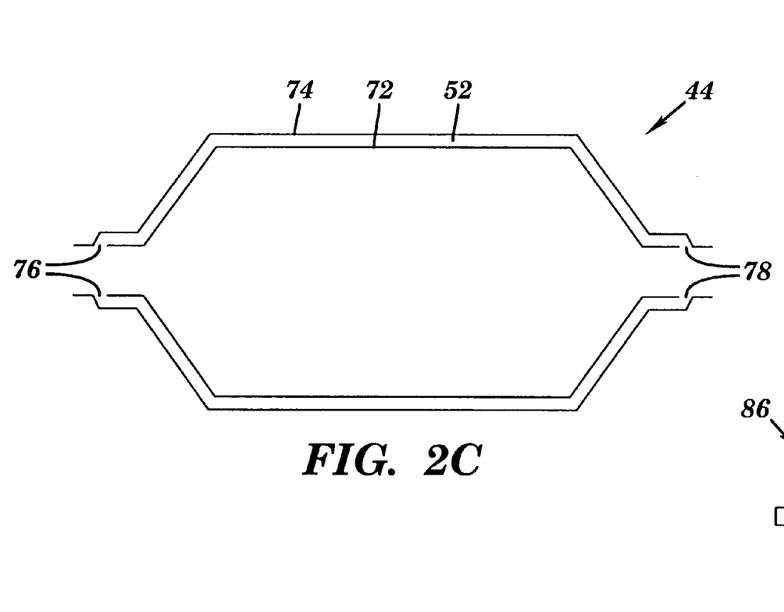

Returning briefly to FIG. 2A, inflatable member 44 is illustrated as including flexible inner wall 48 and flexible outer wall 50, which together enclose cavity 52. FIG. 2C details a suitable configuration for inflatable member 44. Referring now to FIG. 2C, inflatable member 44 is illustrated as including inner balloon 72 (which forms FIG. 2A's flexible inner wall 48) and outer balloon 74 (which forms FIG. 2A's flexible outer wall 50), which together enclose cavity 52. Inner balloon 72 and outer balloon 74 are positioned such that cavity 52 has one or more openings 76 at the proximal end and one or more openings 78 at the distal end of inflatable member 44. Openings 76 and 78 are positioned such that, when inflatable member 44 is secured to outer surface 54 of tubular housing 58, openings 76 are in registration with exit openings 66 of lumens 60 and openings 78 are in registration with openings 68 of central lumen 64.

Although any compliant material can be used for the construction of inflatable member 44's flexible inner wall 48 and flexible outer wall 50 (e.g., inner balloon 72 and outer balloon 74), it will be appreciated that the optimal choice of the material or materials will depend on a variety of factors including, for example, the degree of flexibility or compliancy desired, biocompatibility with the environment in which the apparatus is to be used, and nature of the energy source used in the apparatus. For example, where the energy source is laser light, inflatable member 44's flexible inner wall 48 and flexible outer wall 50 (e.g., inner balloon 72 and outer balloon 74) can be made, for example of a medical grade thermoplastic selected such that the medical grade thermoplastic has minimal absorption at the wavelength of the laser light to be employed. Suitable materials include polyethlenes, teflons, and other thermoplastics or thermosets known to those skilled in the art. It will also be appreciated that the materials from which inflatable member 44's flexible inner wall 48 and flexible outer wall 50 (e.g., inner balloon 72 and outer balloon 74) are made will affect the geometry (e.g., thickness) of cavity 52. Preferably, inner wall 48 and flexible outer wall 50 are configured such that, when inflatable member 44 is inflated, cavity 52 is substantially uniformly thick over at least about 30% (e.g., at least about 40%, at least about 50%, at least about 60%, and/or at least about 70%) of its length. As used here, "substantially uniformly thick" is meant to include those configurations in which the maximum thickness minus the minimum thickness divided by the minimum thickness is less than about 3, such as less than about 2, less than about 1, less than about 0.5, and/or less than about 0.25. However, uniform cavity thickness is not necessary to the apparatus of the present invention. For example, it may even be desirable to have the cavity thicker at the proximal and distal ends, for example, so that stray light or other energy from the energy delivery component is more effectively attenuated by the cooling fluid in these areas, thus protecting tissue not intended for treatment.

As indicated above, inflatable member 44 is secured to outer surface 54 of tubular housing 58. This can be done in any suitable way, such as chemically (e.g., by using a medical grade epoxy (Loctite Corporation Part No. 4981) or other suitable adhesives) or mechanically.

Figure 2D:
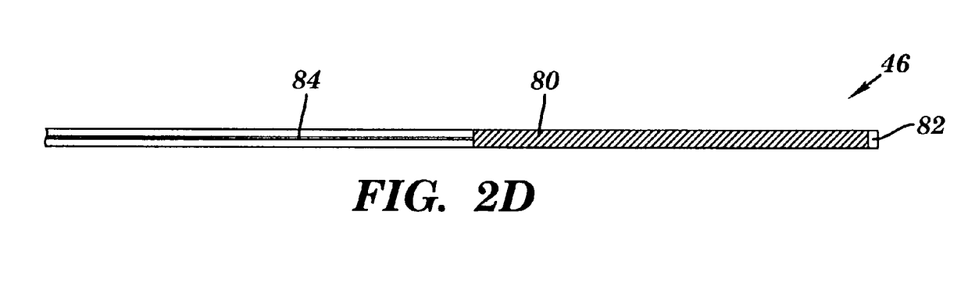

FIG. 2D details one suitable configuration for laser energy delivery component 46. Referring now to FIG. 2D, laser energy delivery component 46 is illustrated as including optical diffusing element 80, reflector 82, and optical waveguide 84. It should be noted that the use of reflector 82 is optional. In operation, when reflector 82 is employed, laser light from a laser light source (not shown) is delivered via waveguide 84 to optical diffusing element 80, and any light which is not diffused by optical diffusing element 80 is reflected back into optical diffusing element 80 by reflector 82. Preferably, the length of optical diffusing element 80 is selected so as to be similar to that of tubular housing 58's optically transparent window section 70. In operation, diffusing element 80 is inserted into tubular housing 58's central lumen 64 such that laser energy delivery component 46's diffusing element 80 is substantially aligned with tubular housing 58's optically transparent window section 70. Examples of suitable laser energy delivery components that can be used in the apparatus of the present invention include those described in U.S. Pat. No. 4,660,925 to McCaughan, Jr., which is hereby incorporated by reference. Alternatively, the laser delivery component can be constructed of one or more optical fibers directed to deliver laser light over the length of tubular housing 58's optically transparent window section 70 and configured so as to emit light in a substantially uniform cylindrical pattern.

Figure 2E:
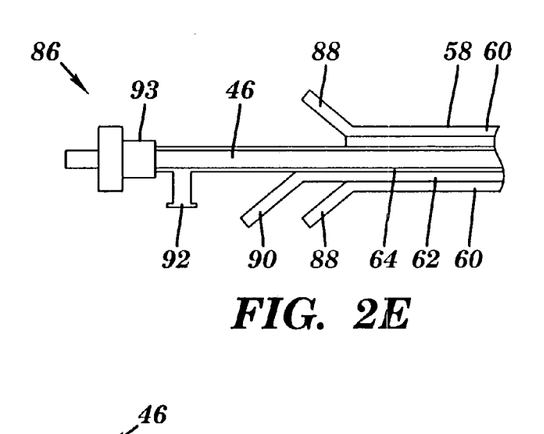

FIG. 2E details a suitable configuration for the proximal end of thermal delivery apparatus 40. Referring now to FIG. 2E, proximal end 86 of thermal delivery apparatus 40 is shown as including one or more lumen openings 88 for the introduction of cooling fluid into lumens 60 of tubular housing 58; one or more lumen openings 90 for the introduction of a gas or liquid into one or more lumens 62 to inflate or otherwise expand interior space 56 of inflatable member 44, an opening 92 in communication with central lumen 64 of tubular housing 58 for exit of the cooling fluid, and Touhy bore connector 93 or other suitable connector for introducing energy delivery component 46 into central lumen 64 of tubular housing 58.

Figure 3A:
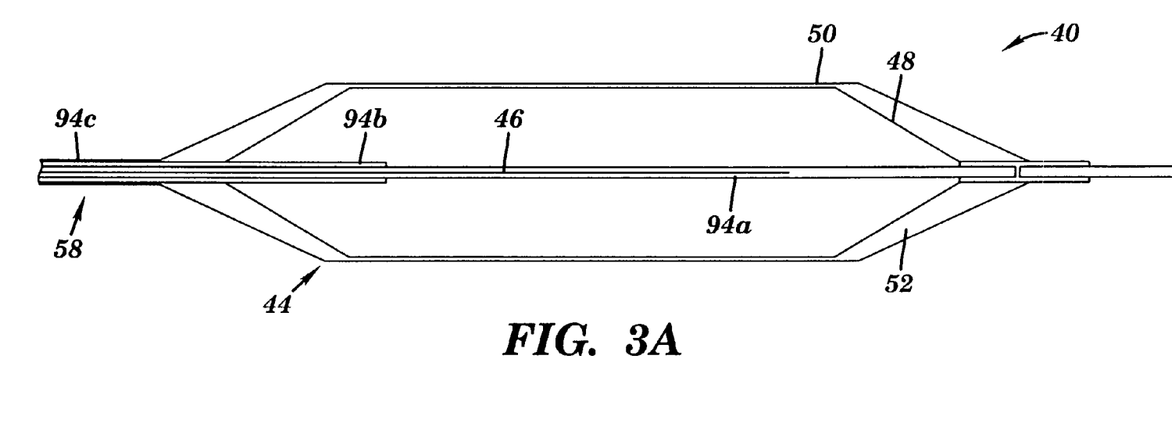
FIG. 3A is a longitudinal sectional view of an apparatus according to the present invention.

FIGS. 3A–3D further illustrate the apparatus of the present invention. In FIG. 3A, apparatus 40 includes inflatable member 44 and an energy delivery component (shown as diffusing tip fiber optic 46). Inflatable member 44 is illustrated as including flexible inner wall 48 and flexible outer wall 50, which together enclose cavity 52. The energy source (i.e., diffusing tip fiber optic 46) is illustrated as being disposed in tubular housing 58. Tubular housing 58 includes transmissive tube 94a which is made of a material, such as polytetrafluoroethylene ("PTFE"), that is transmissive (or substantially transmissive) to light being emitted from diffusing tip fiber optic 46. Diffusing tip fiber optic 46 is disposed in transmissive tube 94a, and transmissive tube 94a is sized such that there is a space (e.g., a first lumen) between diffusing tip fiber optic 46 and transmissive tube 94a thus permitting the flow of cooling fluid alongside diffusing tip fiber optic 46. At its proximal end, tubular housing 58 further includes opaque tube 94b which is made of a material that is opaque (or substantially opaque) to light being emitted from diffusing tip fiber optic 46. Opaque tube 94b is disposed radially around (e.g., concentrically around) transmissive tube 94a. Opaque tube 94b can be sized such that there is a space between transmissive tube 94a and opaque tube 94b; or opaque tube 94b can be sized such that there is no space between transmissive tube 94a and opaque tube 94b; and/or transmissive tube 94a and opaque tube 94b can be unitarily constructed (e.g., by coating transmissive tube 94a with a layer of an opaque material. Also at the proximal end, tubular housing 58 further includes outer tube 94c, which can be made of a transmissive or opaque material and which is disposed radially around (e.g., concentrically around) opaque tube 94b. Outer tube 94c is sized such that there is a space between opaque tube 94b and outer tube 94c (e.g., a second lumen) through which cooling fluid can flow. Opaque tube 94b and outer tube 94c can be made of the same or different materials. For example, each of opaque tube 94b and outer tube 94c can be made of a polyimide resin.

In the preceding discussion with regard to FIG. 3A, tube 94b is referred to as being opaque. It should be noted that FIG. 3A is only illustrative of the present invention and that tube 94b need not be opaque for the apparatus of the present invention to function. Thus, for example, the present invention contemplates embodiments, similar to the one illustrated in FIG. 3A, in which a transmissive tube is substituted for opaque tube 94b.

Figure 3B:
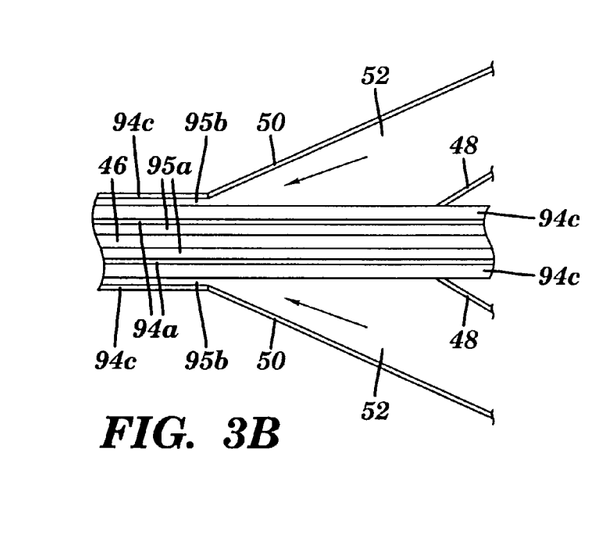
FIGS. 3B and 3C are longitudinal sectional views of the proximal end (FIG. 3B) and distal end (FIG. 3C) of the apparatus shown in FIG. 3A.
Figure 3C:
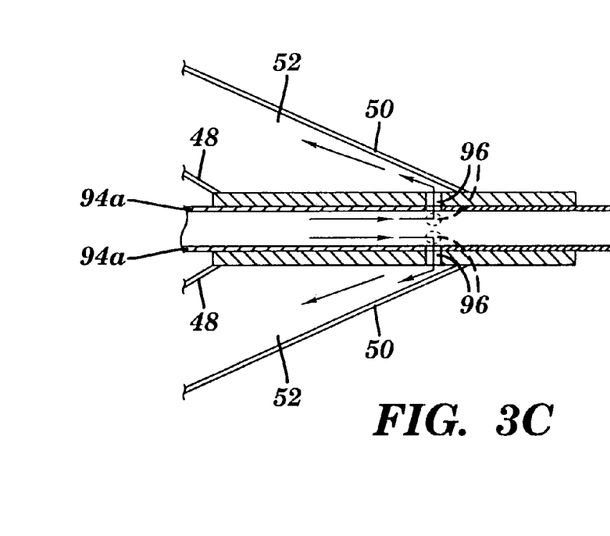

The operation and further details regarding the construction of the apparatus shown in FIG. 3A is illustrated in FIGS. 3B and 3C. More particularly, FIG. 3B shows the proximal end of apparatus 40, and FIG. 3C shows the distal end of apparatus 40. In each of FIGS. 3B and 3C, the direction of flow of cooling fluid is indicated by solid-headed arrows. Referring to FIG. 3B, cooling fluid enters the proximal end of apparatus 40 via a first lumen (shown as passageway 95a), which is bounded by the inner surface of transmissive tube 94a and the outer surface of diffusing tip fiber optic 46. The cooling fluid flows in a distal direction through passageway 95a in contact with the surface of diffusing tip fiber optic 46 and then continues to flow distally through transmissive tube 94a until it reaches the distal end of apparatus 40. Here, as illustrated in FIG. 3C, holes 96 in transmissive tube 94a permit the cooling fluid to exit transmissive tube 94a and enter cavity 52, which is enclosed by flexible inner wall 48 and flexible outer wall 50 of inflatable member 44. The cooling fluid then flows proximally through cavity 52 until it reaches the proximal end of apparatus 40. Turning again to FIG. 3B, at the proximal end of apparatus 40, the cooling fluid in cavity 52 enters a second lumen (shown as passageway 95b), which is bounded by the inner surface of outer tube 94c and the outer surface of opaque tube 94b. The cooling fluid then continues to flow proximally through passageway 95b to exit apparatus 40. It will be noted that, in the embodiment illustrated in FIGS. 3B and 3C, the second lumen (i.e., passageway 95b) is radially disposed around (more particularly, concentrically disposed around) the first lumen (i.e., passageway 95a). It will be further noted that, while the direction of cooling fluid flow in each of FIGS. 3B and 3C is indicated by solid-headed arrows, this is done solely for the purposes of illustration and discussion and that the direction of cooling fluid flow can be reversed.

Figure 3D:
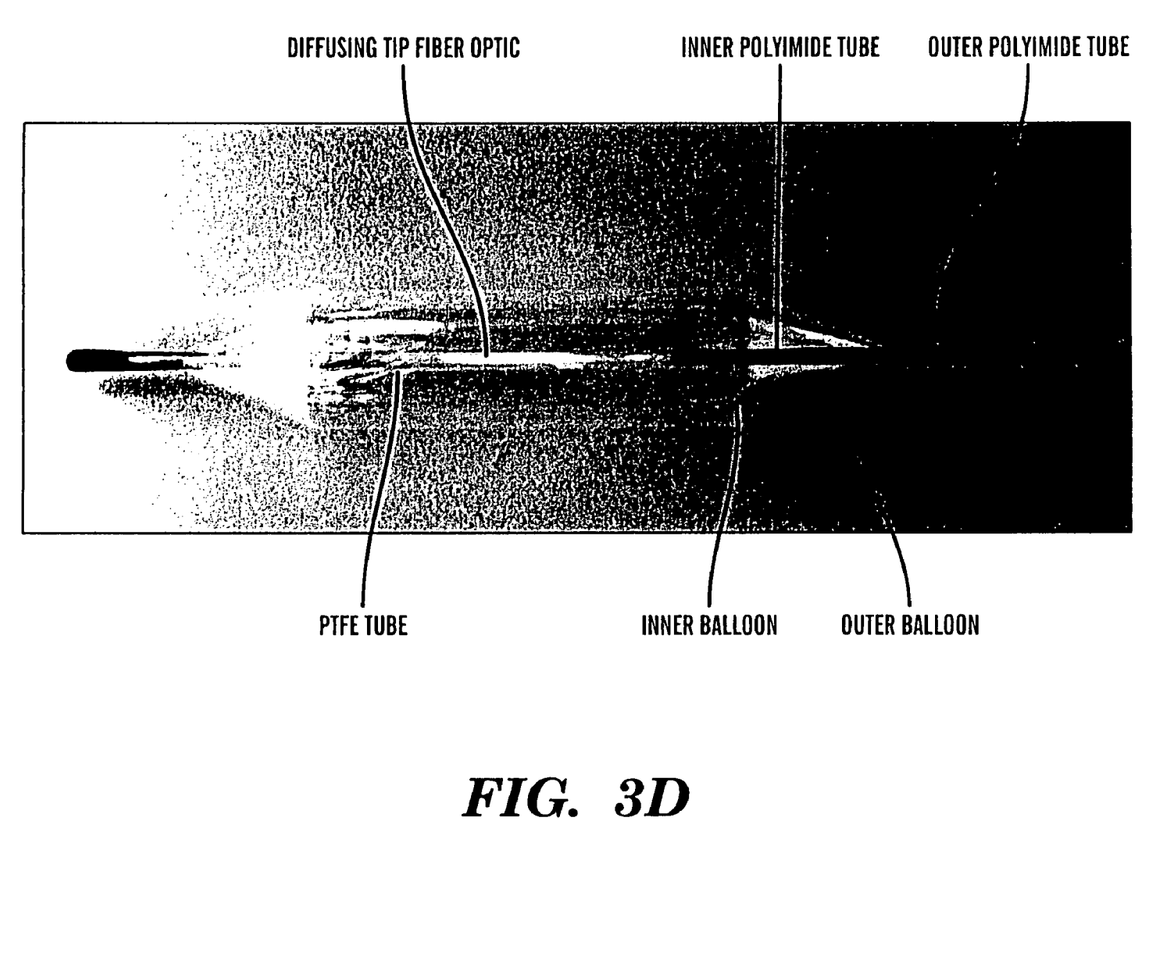
FIG. 3D is an image of an apparatus according to the present invention.
Figure 4A:
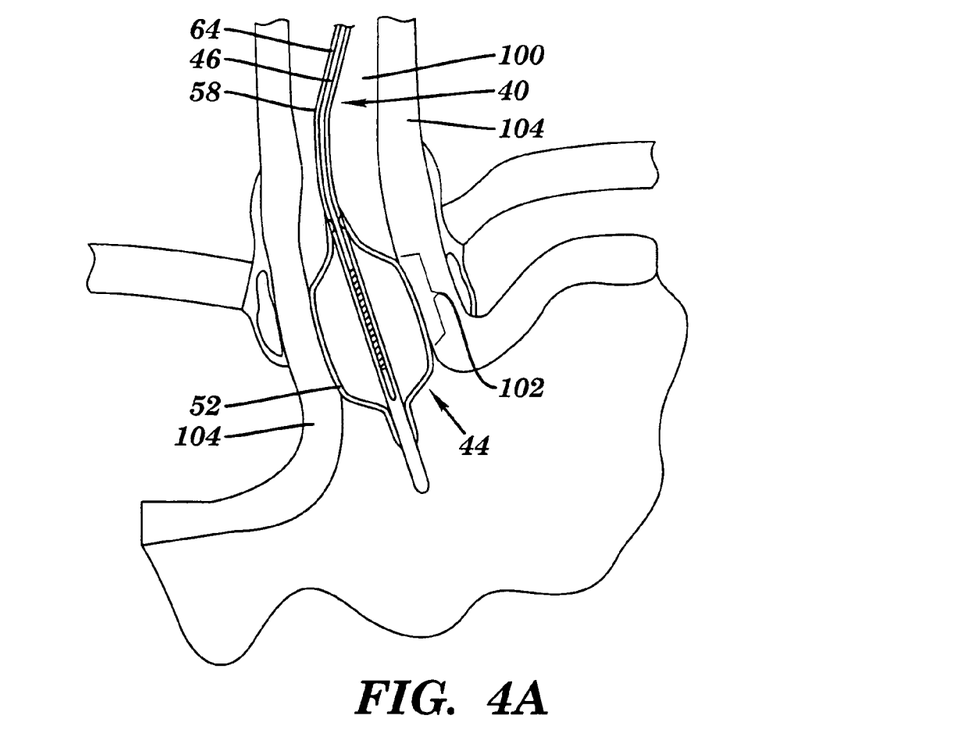
FIGS. 4A and 4B are longitudinal sectional views of an apparatus according to the present invention showing its use for delivering energy to a subject's lower esophageal sphincter.
Figure 4B:
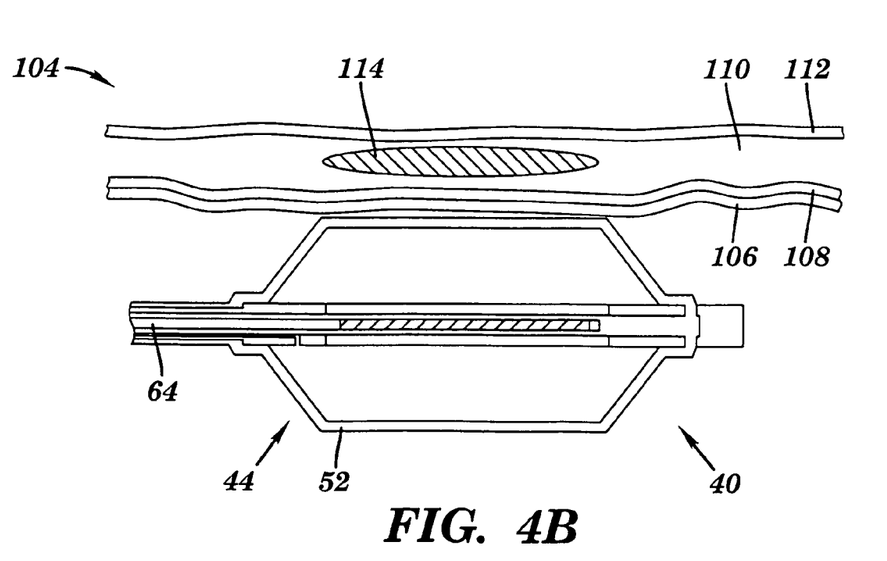
Figure 4C:
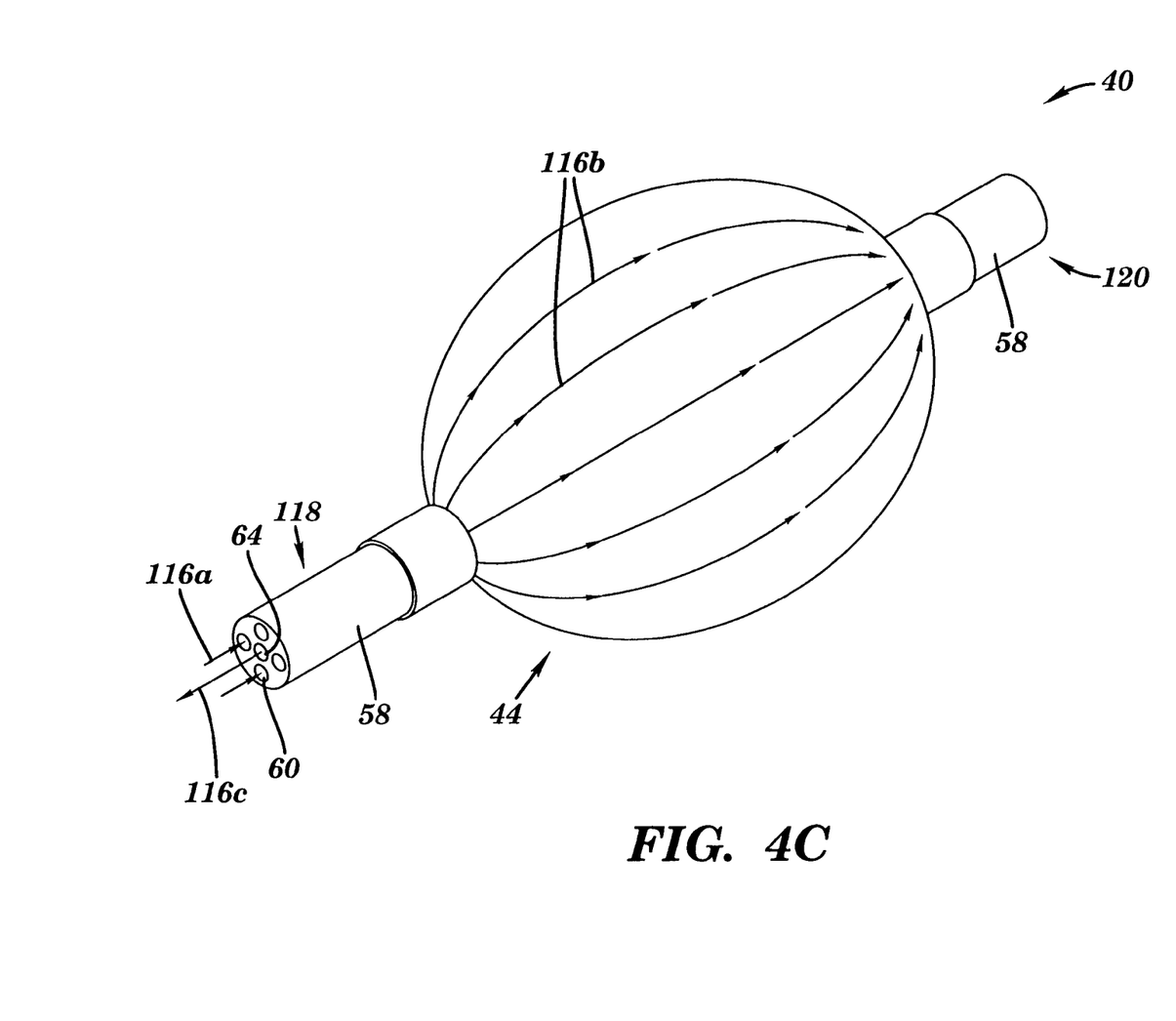
FIG. 4C is a perspective view of an apparatus according to the present invention showing a suitable flow of cooling fluid within the apparatus.

FIG. 3D is an image of a prototype apparatus according to the present invention illustrating one embodiment of an apparatus depicted in FIGS. 4A–4C.

The apparatus of the present invention can be used to deliver energy to tissues, particularly to tissues surrounding a subject's body cavity. Examples of such body cavities include, for example, various parts of the digestive tract, such as the mouth, the esophagus, the stomach, the small intestine, the large intestine, and portions or combinations thereof; various parts of the respiratory tract, such as the nose, the trachea, the bronchi and other parts of the lungs, and portions or combinations thereof; parts of the ear, such as the ear canal; parts of the circulatory system, such as heart chambers, major and minor arteries, major and minor veins, etc.; and parts of various other organs, such as the bladder, the prostate, the kidneys, the pancreas, the liver, the gall bladder, and portions or combinations thereof, as well as their associated ducts. Such tissues can include a surface tissue layer (e.g., a mucosal layer) and one or more subsurface tissue layers (e.g., a muscle layer) which lie beneath the surface tissue layer.

One method of using the apparatus of the present invention, to which method the present invention also relates, involves expanding the inflatable member such that the inflatable member's outer wall contacts the tissue surface; disposing a cooling fluid in the cavity; and delivering energy to the energy delivery component so that at least a portion of the energy delivered to the energy delivery component passes through the inflatable member's inner wall, through the cooling fluid disposed in the cavity, through the inflatable member's outer wall, and into the tissue. The inflatable member can be expanded using any convenient gas or liquid, preferably one which does not significantly absorb the energy delivered to the energy delivery component. In cases where the tissue includes a surface tissue layer (e.g., a mucosal layer) and one or more subsurface tissue layers (e.g., a muscle layer) lying beneath the surface tissue layer, the energy can be selected so as to be preferentially absorbed by at least one of the subsurface tissue layers (e.g., a muscle layer). Cooling fluid can be disposed in the cavity, for example, by circulating the cooling fluid through the cavity while the tissue is being exposed, for example, using a pump or other similar device. Prior to or subsequent to being circulated through the cavity, the cooling fluid can be contacted with the energy delivery component under conditions effective to cool the energy delivery component. Such contact between the energy delivery component and the cooling fluid can be direct or indirect, so long as conductive, convective, and/or radiative cooling of the energy delivery component is effected. The tissue can be exposed for any suitable duration and at any suitable intensity to effect the desired result (e.g., to produce a lesion in an least a portion of the tissue). For example, in the case where the tissue includes a surface tissue layer (e.g., a mucosal layer) and one or more subsurface tissue layers (e.g., a muscle layer) lying beneath the surface tissue layer, exposure intensity, exposure duration, the type of energy (e.g., in the case of electromagnetic energy, the wavelength of the electromagnetic energy), rate of circulation of cooling fluid, and/or other exposure conditions can be adjusted to produce a lesion in at least a portion of at least one of the one or more subsurface tissue layers (e.g., in the muscle layer) and/or to produce a lesion which is substantially confined to the one or more subsurface tissue layers (e.g., to the muscle layer). For purposes of the present invention, a lesion is to be viewed as being substantially confined to the one or more subsurface tissue layers when the ratio of the number of cells undergoing cell necrosis in the one or more subsurface tissue layers to the number of cells undergoing cell necrosis in the surface tissue layer is greater than about 2, such as greater than about 4, greater than about 8, greater than about 16, greater than about 25, and/or greater than about 100. It will be appreciated that the intensity of the energy delivered to the tissue will also depend on the cooling medium's absorption of the energy emitted by the energy delivery component as well as the amount of cooling fluid in contact with the energy delivery component (e.g., the thickness of passageway 95a (FIG. 3B) and the thickness of the cavity enclosed by the inflatable membrane's inner wall and flexible outer wall. The thickness of the cavity enclosed by the inflatable membrane's inner wall and flexible outer wall, in turn, depends on several factors, including the geometry of the inflatable membrane's inner wall and flexible outer wall, the materials from which they are constructed, the positions at which they are attached to the housing and/or the energy delivery component, and the like. The thickness of the cavity enclosed by the inflatable membrane's inner wall and flexible outer wall also depends on the pressure of the cooling fluid within the inflatable membrane's cavity and the pressure used to inflate or otherwise expand (or used to maintain the inflation of) the inflatable membrane.

For example, one way of using the various apparatus illustrated in FIGS. 2A–2E and 3A–3D is described below in connection with FIGS. 4A and 4B.

Referring to FIG. 4A, the thermal delivery apparatus 40 is inserted into esophagus 100 under local anesthesia and positioned under endoscopic or other guidance at the level of lower esophageal sphincter ("LES") 102. Once at the desired position, inflatable member 44 of thermal delivery apparatus 40 is inflated such that inflatable member 44 of thermal delivery apparatus 40 engages walls 104 of esophagus 100. Cooling fluid is introduced into thermal delivery apparatus 40 such that it flows through cavity 52 of inflatable member 44 and returns through central lumen 64 of thermal delivery apparatus 40's tubular housing 58. The temperature, specific heat, and/or flow rate of the cooling fluid can be varied to provide optimum cooling of the esophagus mucosal surface. Optical energy (e.g., laser light) is then delivered through optical delivery component 46 to LES 102. As the skilled artisan will note, FIG. 4A shows optical delivery component 46 delivering optical energy over the entire length of LES 102 in a single treatment. However, the invention can be practiced using a thermal delivery apparatus 40 configured such that optical energy is delivered to only a portion of the LES. Optical delivery component 46 can then be made to mechanically scan the tissue to create a homogenous lesion along any desired length of the LES. Such mechanical scanning can be carried out, for example, by moving optical delivery component 46 axially relative to central lumen 64 of the tubular housing 58 or by deflating inflatable member 44, moving thermal delivery apparatus 40 relative to LES 102, and repeating the procedure.

As one skilled in the art will appreciate, the time and intensity of exposure and the degree of cooling can be varied depending on the desired objective. For example, as indicated above, the apparatus and method of the present invention can be used to treat tissues which include a surface tissue layer and one or more subsurface tissue layers which lie beneath the surface tissue layer. In such cases, it can be desirable to adjust the rate at which the tissue is cooled (e.g., by adjusting the temperature and/or flow rate of the cooling fluid circulating through the inflatable member's cavity), to adjust the intensity of the exposure, and/or to select the type of energy (e.g., the wavelength of light energy) so that the energy is preferentially absorbed by at least one of the subsurface tissue layers.

FIG. 4B illustrates thermal delivery apparatus 40 positioned against esophagus wall 104. Esophagus wall 104 includes inner mucosal layer 106, submucosal layer 108, smooth muscle layer 110, and outer adventitial layer 112. During the treatment process, apparatus 40 is designed to cool inner mucosal layer 106 and submucosal layer 108 through convective and/or conductive heat transfer with fluid flowing through cavity 52 of apparatus 40's inflatable member 44. By optimizing the selection of wavelength and dosimetry, laser delivery component 64 of apparatus 40 can produce a controlled thermal lesion (e.g., thermal lesion 114) whose boundaries are limited or otherwise substantially confined to a particular tissue layer, such as smooth muscle layer 110. For example, using the apparatus of the present invention, a lesion can be produced such that the lesion is substantially confined to the muscle layer (i.e., without substantial thermal or mechanical damage to inner mucosal layer 106 or submucosal layer 108). For purposes of the present invention, a lesion is to be deemed to be substantially confined to the muscle layer when the ratio of the number of cells undergoing cell necrosis in the muscle layer to the number of cells undergoing cell necrosis in the overlying layers (e.g., in the inner mucosal and submucosal layers) is greater than about 2, such as greater than about 4, greater than about 8, greater than about 16, greater than about 25, and/or greater than about 100.

FIG. 4C illustrates one suitable flow path of cooling fluid through thermal delivery apparatus 40. In FIG. 4C, flow of cooling fluid is indicated by the arrows 116a, 116b, and 116c. Briefly, cooling fluid is introduced (as indicated by arrows 116a) through one or more lumens 60 at proximal end 118 of tubular housing 58 and flows (as indicated by arrows 116b) through the cavity of inflatable member 44, which, in operation, is in contact with the mucosal layer of the esophagus. At distal end 120 of tubular housing 58, the medium flows into central lumen 64 (for example, via openings 68 and 78, as illustrated in FIGS. 2B and 2C), and then flows in a proximal direction through central lumen 64 (as indicated by arrows 116c). Since the laser delivery component is disposed in central lumen 64, the cooling fluid, while flowing in a proximal direction through central lumen 64, is in contact with the laser delivery component. Thus, in this embodiment of the present invention, both the mucosal layer and the laser delivery component are cooled by the flow of a single cooling fluid. Moreover, by adjusting the size of the cavity and the size of the central lumen, the cooling fluid can be confined to two relatively thin layers (one near the laser delivery component and the other near the tissue surface), thus minimizing the path length of laser light (or other form of energy) through the cooling fluid and the consequential attenuation of laser light (or other form of energy) by the cooling fluid. The cooling fluid can be, for example, room temperature water or saline solution, cooled water or saline solution, other room temperature or cooled fluids, or cooled gas, such as cooled air, nitrogen, and/or carbon dioxide. The cooling fluid can be one which does not absorb a significant amount of the energy being delivered via the energy delivery component, or it can be one which absorbs a significant amount of the energy being delivered via the energy delivery component. For the purposes of the present invention, cooling fluid which absorbs more than about 2% (e.g., more than about 5%, more than about 10%, more than about 20%, and/or more than about 40%) of incident energy per centimeter of path length is to be deemed as absorbing a significant amount of the energy being delivered via the energy delivery component. For example, when a near-infrared laser light is used, the cooling fluid can be a gas, such as a cooled gas; and, when the visible laser light (e.g., from a Kr or Ar laser) is used, the cooling fluid can be a cooled liquid (e.g., cooled water or cooled saline solution).

After treatment, thermal delivery apparatus 40 is removed, and the sphincter is allowed to heal. It is believed that, upon healing, the lesion in the smooth muscle layer provides an increase in resistance to sphincter relaxation and subsequent reflux.

During therapy, one or more feedback variables can be monitored as indicators that adequate damage level has been obtained. Such indicators can include, for example, surface temperature, electrophysiologic signals, tissue electrical impedance, tissue acoustic impedance, optically monitored calorimetric changes in tissue constituents, and mechanical properties (e.g., tissue modulus or compliance).

Accordingly, the apparatus of the present invention can also include one or more components for measuring one or more of the feedback indicators mentioned above.

For example, the apparatus can include electrodes on the surface of the inflatable member which, in operation, are in contact with the tissue surface (e.g., of the LES) and which are used to monitor the electrical impedance of the tissue (e.g., of LES tissue) during therapy. For example, the electrodes can be used to measure electrical impedance, and the electrodes can be connected to a suitable display for reporting electrical impedance to the operator. The electrodes can additionally or alternatively be coupled to a mechanism which, rather than reporting electrical impedance in absolute terms, reports a change in electrical impedance and/or indicates when a "goal" electrical impedance measurement is achieved.

Alternatively or additionally, the apparatus of the present invention can also include one or more components for measuring pressure changes. For example, the apparatus can include a pressure transducer and a pressure modulator which are connected to the cooling fluid circuit of the apparatus. During operation of such an apparatus, fluid flow can be stopped (during therapy or at intervals in between therapeutic pulses), and a series of induced pressure changes can be imparted to the fluid with the pressure modulator. The signals received by the pressure transducer would be dependent on the compliance of the inflatable member, tubing system, and tissue (e.g., the esophageal wall) which is in contact with the apparatus. The portion of the signal received by the pressure transducer due to compliance of the inflatable member and tubing system can be determined by measuring the response to appropriate pressure modulation input signals. Changes in the detected compliance can then be translated into changes in tissue (e.g., esophageal wall) compliance, and such changes in tissue compliance can be reported to the operator or used as a means of automatic therapy control.

Still alternatively or additionally, the apparatus of the present invention can include an acoustic transducer/receiver located at the proximal end of the inflatable member. In operation, the apparatus would be placed in the desired location, and the inflatable member would be inflated or otherwise expanded so as to contact the tissue to be treated. Then, prior to beginning therapy (i.e., prior to energizing the apparatus's energy delivery component), the acoustic transducer/receiver would be energized to emit an acoustic pulse at a single frequency (or a series of pulses at several different frequencies), and the acoustic energy re-radiated by the tissue in contact with the inflatable member would be recorded. Therapy would then be commenced (i.e., the apparatus's energy delivery component would be energized). During the therapy (e.g., at a variety of time intervals), the acoustic transducer/receiver would be energized to emit an acoustic pulse at a single frequency (or a series of pulses at several different frequencies), and the acoustic energy re-radiated by the treated tissue in contact with the inflatable member would be recorded. The energy re-radiated by the tissue after some exposure dose would be compared to the energy re-radiated by the tissue prior to treatment, and changes can be used to guide the operator in determining when an optimal or sufficient therapeutic dose has been achieved.

Still alternatively or additionally, the apparatus of the present invention can include one or more components for measuring light reflected from or absorbed by the tissue being treated to examine the extent of necrosis and to determine when a sufficient therapeutic dose has been achieved.

The apparatus of the present invention can further include one or more components which assist in the placement and/or maintaining the position of the apparatus during treatment.

Figure 5A:
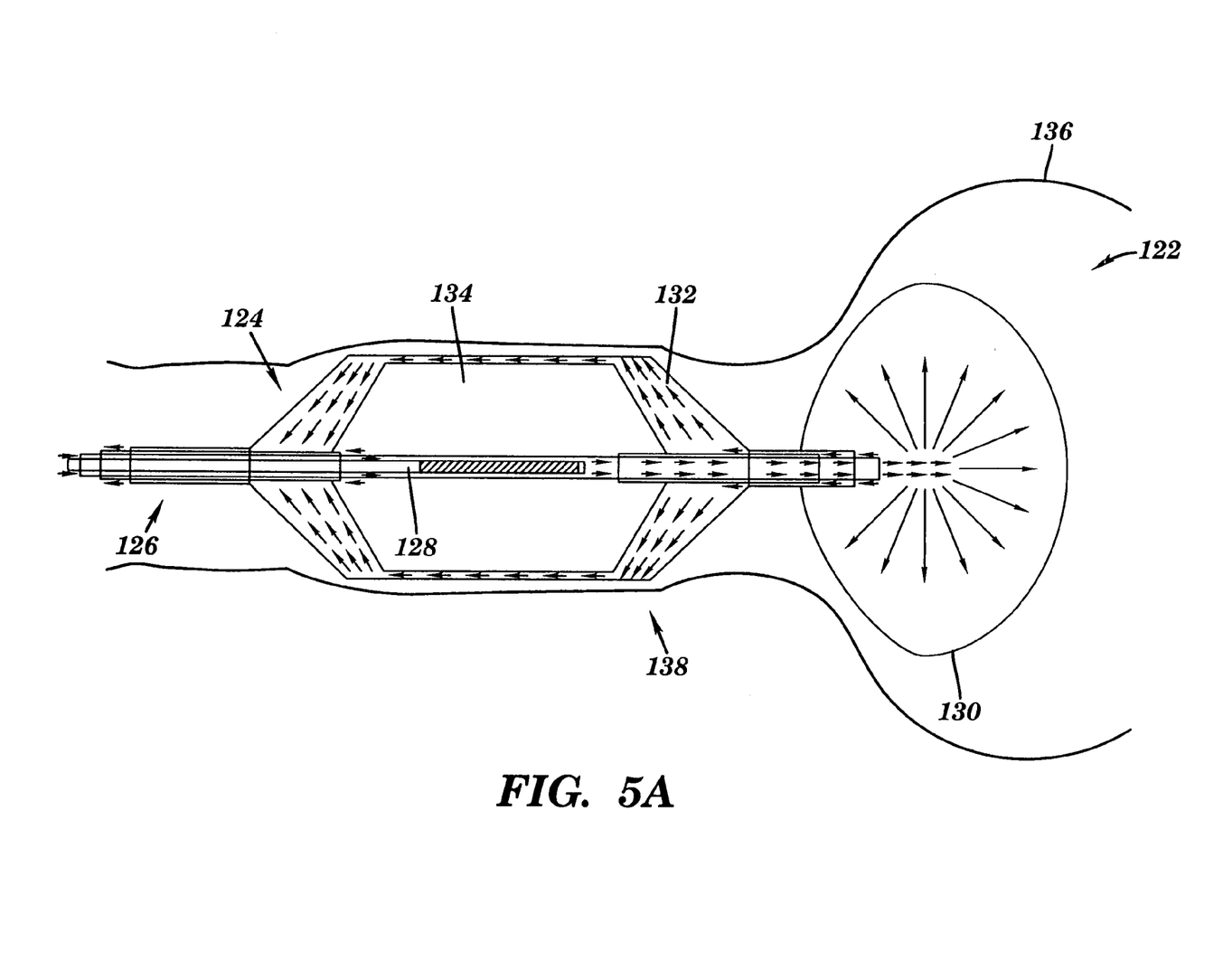
FIGS. 5A and 5B are longitudinal sectional views of apparatus according to the present invention showing their use for delivering energy to a subject's lower esophageal sphincter.
Figure 5B:
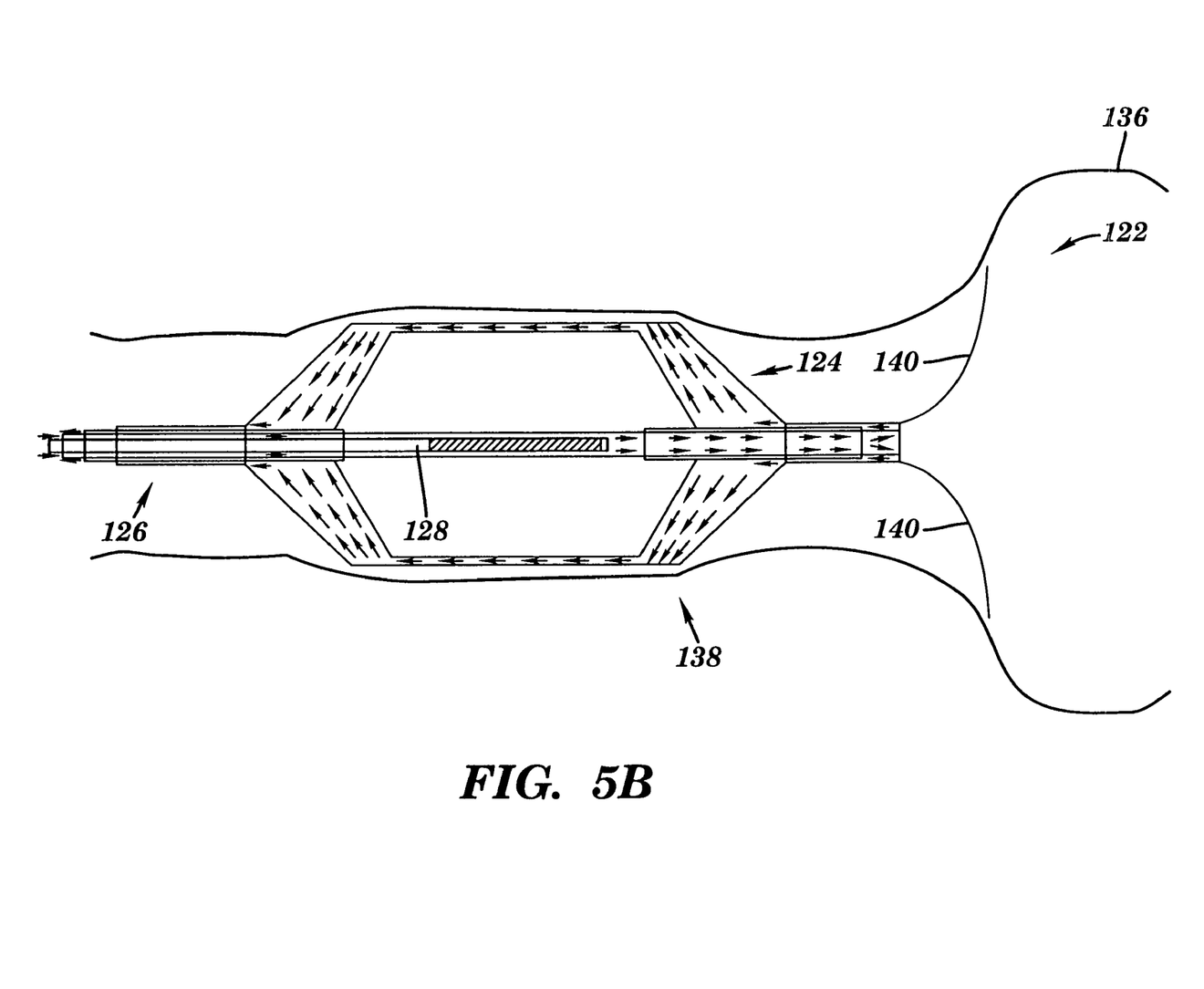

Such apparatus are illustrated in FIGS. 5A and 5B. Referring to FIG. 5A, apparatus 122 is shown as including inflatable member 124, tubular housing 126, and energy delivery component 128 (e.g., a component for delivering laser energy) disposed in tubular housing 126. Apparatus 122 further includes balloon 130 at the distal end. Balloon 130 includes an inlet to permit inflation thereof. Inflation can be achieved by means of having the inlet of balloon 130 in fluid communication with the cooling fluid which contained in inflatable member 124's cavity 132, as illustrated in FIG. 5A. Alternatively, the inlet of balloon 130 can be in fluid communication with the gas of liquid contained in space 134 (i.e., the gas of liquid used to inflate inflatable member 124), or in fluid communication with a separate source of pressurized gas or liquid via, for example, a separate lumen contained in tubular housing 126. For example, when used to deliver energy to the esophageal sphincter (e.g., when treating GERD), the operator places the distal end of apparatus 122, with inflatable member 124 and balloon 130 in a deflated state, into stomach 136. Balloon 130 is then inflated, and apparatus 122 is moved proximally. Since balloon 130, in its inflated state, cannot pass through LES 138, it remains stomach 136. Thus, after filling balloon 130 and retracting apparatus 122 proximally until balloon 130 engages the LES/stomach junction, the position of energy delivery component 128 relative to the LES/stomach junction would be defined. By adjusting the distance between balloon 130 and energy delivery component 128, energy delivery component 128 can be positioned more exactly for thermal treatment of LES 138. Alternative to the use of balloon 130 to assist in the placement and/or maintaining the position of the apparatus during treatment, retractable arms 140 can be employed, as illustrated in FIG. 5B. In FIGS. 5A and 5B indicate one suitable path for the flow of cooling fluid through apparatus 122. However, it will be appreciated that the direction can be reversed and that other paths are suitable.

The present invention also relates to a method for reducing reflux of a subject's stomach contents into the subject's esophagus. The method of the present invention can be practiced on any suitable subject, e.g. a human who suffers from GERD or whose lower esophageal sphincter otherwise fails to function properly. The method includes cooling a mucosal layer of the subject's lower esophageal sphincter and exposing the subject's lower esophageal sphincter to laser radiation.

Each of the cooling and exposing steps can be carried out continuously or intermittently, or cooling can be commenced and completed prior to commencing exposure, or cooling can be commenced prior to exposure and continued for the entire duration of the exposure step.

The subject's lower esophageal sphincter is exposed to laser radiation under conditions effective to cause cellular necrosis in the subject's lower esophageal sphincter and under conditions effective to cause a thermal lesion in the subject's lower esophageal sphincter. Exposure can be carried in any suitable way, for example, by introducing a optical waveguide (e.g., a fiber optic) via the subject's oral cavity into the subject's esophagus and positioning the tip of the optical waveguide at the level of the LES. The optical waveguide is coupled optically to a source of laser light (e.g., a laser), and the frequency of the laser light can be chosen so as to be absorbed by the tissue of the LES. Preferably, the frequency of the laser light is chosen so as to be preferentially absorbed by the LES's muscle layer (e.g., the LES's smooth muscle layer).

Cooling can be limited to the mucosal layer, or it can be carried out such that other layers (e.g., a submucosal layer) of the LES are cooled. In certain circumstances it may also be desirable to also cool the LES's smooth muscle layer or a portion thereof (i.e., in addition to cooling the LES's mucosal layer). Cooling of the lower esophageal sphincter's mucosal layer (and, optionally, other lower esophageal sphincter layers) can be carried out by any suitable method, such as, for example, by circulating cooling fluid (e.g., a gas or a liquid) through double-walled balloon inflated so as to be in contact with the subject's lower esophageal sphincter. The depth of cooling can be controlled for example by controlling the rate of cooling fluid circulation, the temperature of the cooling fluid, and the like. Preferably, exposure and cooling are adjusted so as to form a thermal lesion which is substantially confined to the lower esophageal sphincter's smooth muscle layer.

Although preferred embodiments have been depicted and described in detail herein, it will be apparent to those skilled in the relevant art that various modifications, additions, substitutions and the like can be made without departing from the spirit of the invention and these are therefore considered to be within the scope of the invention as defined in the claims which follow.

What is claimed is:

1. A method for delivering energy to a tissue having a tissue surface, said method comprising:
   providing an apparatus comprising an energy delivery component and an inflatable member disposed around the energy delivery component, wherein the inflatable member comprises an inner wall and an outer wall, wherein the inflatable member's inner wall is flexible, wherein the inflatable member's outer wall is flexible, and wherein the inflatable member's inner wall and the inflatable member's outer wall enclose a cavity therebetween;
   expanding the inflatable member such that the inflatable member's outer wall contacts the tissue surface;
   disposing a cooling fluid in the cavity; and
   delivering energy to the energy delivery component so that at least a portion of the energy delivered to the energy delivery component passes through the inflatable member's inner wall, through the cooling fluid disposed in the cavity, through the inflatable member's outer wall, and into the tissue.

2. A method according to claim 1, wherein the tissue is a lower esophageal sphincter.

3. A method according to claim 1, wherein the energy delivery component is an optical waveguide coupled to a light source.

4. A method according to claim 1, wherein the energy delivery component is fiber optic coupled to a monochromatic light source.

5. A method according to claim 1, wherein the energy delivery component is fiber optic coupled to a laser light source.

6. A method according to claim 1, wherein the tissue comprises a surface tissue layer and one or more subsurface tissue layers lying beneath the surface tissue layer and wherein the energy is selected so as to be preferentially absorbed by at least one of the subsurface tissue layers.

7. A method according to claim 1, wherein the tissue comprises a mucosal layer and a muscle layer lying beneath the mucosal layer and wherein the energy is selected so as to be preferentially absorbed by the muscle layer.

8. A method according to claim 1, wherein said disposing a cooling fluid in the cavity is carried out by circulating the cooling fluid through the cavity during said delivering.

9. A method according to claim 1, wherein said delivering is carried out for a period of time sufficient to produce a lesion in an least a portion of the tissue.

10. A method according to claim 1, wherein the tissue comprises a mucosal layer and a muscle layer lying beneath the mucosal layer, wherein said delivering is carried out under conditions effective to produce a lesion in at least a portion of the muscle layer, and wherein the lesion is substantially confined to the muscle layer.

11. A method according to claim 1 further comprising:
detecting a change in a property of the tissue resulting from energy delivered to the tissue by the apparatus.

12. A method for delivering energy to a tissue comprising a surface tissue layer and one or more subsurface tissue layers lying beneath the surface tissue layer, said method comprising:
cooling at least the tissue's surface tissue layer with a cooling fluid; and
exposing the tissue to laser energy such that the laser energy is preferentially absorbed by at least one of the subsurface tissue layers.

13. A method according to claim 12, wherein the tissue comprises a surface tissue layer, a mucosal layer lying beneath the surface tissue layer, and a muscle layer lying beneath the mucosal layer and wherein the laser energy is selected so as to be preferentially absorbed by the muscle layer.

* * * * *